United States Patent
Eyupoglu

(10) Patent No.: US 12,310,358 B2
(45) Date of Patent: May 27, 2025

(54) FIGHTING AGAINST VARROA PARASITE IN BEEKEEPING USING A NATURAL FORMULATION COMPRISING ESSENTIAL OILS AND WOOD VINEGAR

(71) Applicant: Istanbul Medipol Universitesi, Istanbul (TR)

(72) Inventor: Ozan Emre Eyupoglu, Istanbul (TR)

( * ) Notice: Subject to any disclaimer, the term of this patent is extended or adjusted under 35 U.S.C. 154(b) by 459 days.

(21) Appl. No.: 17/770,963

(22) PCT Filed: Nov. 12, 2020

(86) PCT No.: PCT/TR2020/051092
§ 371 (c)(1),
(2) Date: Apr. 21, 2022

(87) PCT Pub. No.: WO2021/096475
PCT Pub. Date: May 20, 2021

(65) Prior Publication Data
US 2022/0369626 A1    Nov. 24, 2022

(30) Foreign Application Priority Data

Nov. 13, 2019   (TR) .................. 2019/17612

(51) Int. Cl.
| | | |
|---|---|---|
| *A01N 25/18* | (2006.01) | |
| *A01N 65/22* | (2009.01) | |
| *A01N 65/28* | (2009.01) | |
| *A24F 40/65* | (2020.01) | |

(52) U.S. Cl.
CPC .............. *A01N 25/18* (2013.01); *A01N 65/22* (2013.01); *A01N 65/28* (2013.01); *A24F 40/65* (2020.01)

(58) Field of Classification Search
None
See application file for complete search history.

(56) References Cited

U.S. PATENT DOCUMENTS 6,646,014 B2 *  11/2003  Watkins ................ A01N 37/04
                                                        424/408
2009/0131539 A1    5/2009  Schutz et al.

FOREIGN PATENT DOCUMENTS

| DE | 102014110009 B4 * | 2/2018 | ............... A61L 2/00 |
| WO | 2013155438 A1 | 10/2013 | |
| WO | 2020172750 A1 | 9/2020 | |

OTHER PUBLICATIONS

Tutun et al. "Plant essential oils used against some bee diseases," Turkish Journal of Agriculture—Food Science and Technology 6 (1):34-45, 2018 (Year: 2018).*
Google translation DE 10-2014-110009 A1, printed 2024 (Year: 2024).*
International Search Report for corresponding PCT/TR2020/051092, dated Mar. 12, 2021.
Written Opinion of the International Searching Authority for corresponding PCT/TR2020/051092, dated Mar. 12, 2021.
Oliver, R., "IPM 7 Fighting Varroa The Arsenal: Natural Treatments—Part 1" and "IPM 7 Fighting Varroa The Arsenal: Natural Treatments—Part 2", accessed at http://scientificbeekeeping.com/the-arsenal-natural-treatments-part-1/ and http://scientificbeekeeping.com/ipm-7-the-arsenal-natural-treatments-part-2/, respectfully, Publication dates: Aug. 2007, Sep. 2007. (Collectively D2 in ISR and Written Opinion).
Demirel et al., "Varroa Mücadelesínde Sentetík Ve Organík Akarísítlerín Kullanim Olanaklari" Uludag Bee Journal 2019, pp. 96-109. (D5 in ISR; English Abstract provided; see Written Opinion).

* cited by examiner

Primary Examiner — Marianne C Seidel
Assistant Examiner — Alissa Prosser
(74) Attorney, Agent, or Firm — Egbert, McDaniel & Swartz, PLLC

(57) ABSTRACT

An essential oil mixture for fighting *varroa* parasites, the essential oil mixture has 15% to 25% wood vinegar by volume of the entire mixture, 25% to 35% thyme oil by volume of the entire mixture, 25% to 35% aniseed oil by volume of the entire mixture, 8 to 13% clove oil by volume of the entire mixture, 3 to 8% cardamom oil by volume of the entire mixture, and 3 to 8% peppermint oil by volume of the entire mixture. The essential oil mixture is placed in a container such that vapors from the essential oil mixture are released in an area adjacent to the vaporizer device.

13 Claims, No Drawings

FIGHTING AGAINST VARROA PARASITE IN BEEKEEPING USING A NATURAL FORMULATION COMPRISING ESSENTIAL OILS AND WOOD VINEGAR

TECHNICAL FIELD

The present invention relates to an essential oil mixture suitable for use in fighting against *Varroa* parasites that significantly harm beekeeping in our country, and to a kit containing said oil mixture.

PRIOR ART

Bees have a very short life span. They live in the spring and summer and they cannot survive more than 40-50 days. Except for the hive, no member of the family can live outside for a long time. Bee colonies consist of a single queen and tens of thousands of working bees [1]. The quality of bee colonies increases as the number of individuals increase, and top quality is reached in strong families with tens of thousands of working bees. In strong families, it is easy for bees to maintain the necessary temperature and humidity conditions in the hive and to endure various diseases and adverse environmental effects [1]. Bees are susceptible to a variety of diseases. Contagious bee diseases can be difficult for the beekeeper. Some insects, mites, rodents and birds also often weaken or even destroy bee colonies [2]. The causative agents of bee diseases are bacteria, viruses and parasites. Parasites live and feed in the bee colony [2]. If not intervened in time, the bee family will weaken and may die. Parasites of a bee family include Varroas, wax moths, earworms, some insects, mites, and mice [2]. All of them live in the bee's hive for a long period of time and they feed on beeswax, honey, hive material, bees and corpses of their larvae [3].

The *Varroa* parasite disease, which is described as the most terrifying disease of bees, continues to progress and change its pathogenicity, despite over 40 years of study and seeking ways to cope with it [4].

Although Varroas have been known in our country since 1964, they are among the category B quarantine diseases registered in Asia, Europe, North and South America and North African countries [5]. *Varroa* mite sizes are one millimeter in length and one and a half millimeters in width. The color of a young *Varroa* is milky white, while the color of an adult *Varroa* is brown. *Varroa* has four pairs of seven-piece short and strong legs with sucking hairs that attach to the bee. The *Varroa* mite settles between the breast and abdomen of the bee. They feed on the hemolymph in male bees and queen bees [5].

Bees with *Varroa* are a crucial problem for beekeepers and they increase the complexity of care for the bee hive. *Varroa* parasites cause the birth of bees with various deformations, thus reducing the life span of the queens [4].

Monitoring should be performed to identify bee infections or pests. Especially in fighting against *Varroa* parasite, combined parasite decontamination methods that contain physical and chemical tools in a complex should be used appropriately for different situations and seasons. In case of misuse, drug residues may accumulate in the hive and the parasite can get used to the drug [6]. Different experiments have been carried out to combat *Varroa*. A total of 176 experiments were conducted using 3200 female *Varroa* mites and 4100 worker bees [7]. Honey bees and *Varroa* mites were kept in a pool area having a volume of 1160 cm3, poor ventilation, 80-86% relative humidity, and a thermostat that was fixed at 30-33° C. The aqueous extract obtained from the freshly collected thyme and its leaves before the flowering phase was sprayed with the evaporation technique (by fumigation or sublimation) at a dose of 1 mL per pool for 15-17 days. Thyme water caused death of 66.6% of ticks and 25.7% of bees. Experiments have shown that thyme has very strong insecticidal properties [8].

Considering the prior art, it is observed that new agents are needed to reduce the number of *Varroa* parasites/ticks in the colony to a level that will not harm the colony and that should not adversely affect bee welfare while fighting against *Varroa* parasites/ticks.

DETAILED DESCRIPTION OF THE INVENTION

As a result of their studies, the inventors have developed an essential oil mixture suitable for being used in fighting against *Varroa* parasites, said mixture contains;
15%-25% wood vinegar by volume
25%-35% thyme oil by volume
25-35% aniseed oil by volume
8-13% clove oil by volume
3-8% cardamom oil by volume
3-8% peppermint oil by volume.

The term "essential oil" used within the scope of the invention refers to hydrophobic liquids containing volatile chemicals in a plant's structure in concentrated form.

As a result of their studies, the inventors have achieved a synergistic mixture that has a superior effect in fighting against the *Varroa* parasite by using the components that form the essential oil mixture according to the invention in specified amounts and in combination. For example, while the number of *Varroa* parasites destroyed by using aniseed essential oil alone was 14% compared to the total number of parasites, it was found that 70% *Varroa* parasites were killed with the composition according to the invention.

According to a preferred embodiment of the invention, an essential oil mixture suitable for use in fighting against *Varroa* parasites consists of;
20% wood vinegar by volume
30% thyme essential oil by volume
30% aniseed essential oil by volume
10% clove essential oil by volume
5% cardamom essential oil by volume, and
5% peppermint essential oil by volume.

In another aspect, the invention relates to a kit suitable for use in fighting against *Varroa* parasites; said kit comprises a) an essential oil mixture according to the invention and b) a vaporizer device.

In the kit according to the invention, the essential oil mixture can be housed in a separate container, said container can be placed in the vaporizer device before use, or said container can be opened before use and the essential oil mixture can be transferred to a chamber in the vaporizer device.

In one embodiment of the invention, the essential oil mixture can be incorporated into the kit by soaking it with a mat, preferably a copper-containing mat, suitable for use in liquid vaporizers.

The vaporizer device according to the invention can be of any shape and structure that enables the essential oil mixture to evaporate by heating and then allows the formed vapors to be released out of the device. All liquid vaporizers available in the prior art, for example;

essential oil vaporizers, e-cigarettes, mosquito repellent electro-liquid devices can be used in the kit according to the invention.

In another aspect, the invention relates to a method to be used in fighting against *Varroa* parasites, said method includes the steps of;

(a) placing the essential oil mixture containing 15%-25% wood vinegar by volume, 25%-35% thyme oil by volume, 25%-35% aniseed oil by volume, 8-13% clove oil by volume, 3-8% cardamom oil by volume, 3-8% peppermint oil by volume in the vaporizer device, (b) leaving the vaporizer device next to or above the bee hive in working condition.

The process of placing the essential oil mixture mentioned in step (a) of the method according to the invention into the vaporizer device can be carried out by; i) placing the oil mixture in a chamber in the vaporizer device, or ii) placing the container containing the oil mixture into the vaporizer device, or iii) placing the mat impregnated with the essential oil mixture into the vaporizer device.

In a preferred embodiment of the invention, in the method according to the invention, the vaporizer device can be operated manually by an on-off button, located on the device or by connecting the device to an electrical source, or it can be operated by an application that can be connected to the vaporizer device via Bluetooth™ or a wireless connection.

In another aspect, the invention is related to the use of an essential oil mixture containing 15%-25% wood vinegar by volume, 25%-35% thyme oil by volume, 25%-35% aniseed oil by volume, 8-13% clove oil by volume, 3-8% cardamom oil by volume, 3-8% peppermint oil by volume in fighting against *Varroa* parasite.

A preferred embodiment of the invention is related to the use of an essential oil mixture consisting of 20% wood vinegar by volume, 30% thyme essential oil by volume, 30% aniseed essential oil by volume, 10% clove essential oil by volume, 5% cardamom essential oil by volume, and 5% peppermint essential oil by volume in fighting against *Varroa* parasite.

The embodiments of the invention can be combined when technically applicable. The embodiments were described here to include certain features/elements. The disclosure also covers other implementations that essentially contain or consist of said features/elements.

Patents and applications and similar technical references are incorporated herein by reference. The applications specifically and explicitly described herein may serve as a basis for a disclaimer, alone or in combination with one or more other applications.

REFERANSLAR

[1] Brutscher L., Baer B., & Niño E. (2019). Putative Drone Copulation Factors Regulating Honey Bee (*Apis mellifera*) Queen Reproduction and Health: A Review. Insects, 10(1), 8, doi:10.3390/insects10010008.

[2] Abou-Shaara H. F., & Staron M. (2019). Present and future perspectives of using biological control agents against pests of honey bees. Egyptian Journal of Biological Pest Control, 29(1), doi:10.1186/s41938-019-0126-8.

[3] Chandler D., Sunderland K. D., Ball B. V., & Davidson G. (2001). Prospective Biological Control Agents of *Varroa destructor* n. sp., an Important Pest of the European Honeybee, *Apis mellifera*. Biocontrol Science and Technology, 11(4), 429-448, doi:10.1080/09583150120067472

[4] Thoms C. A., Nelson K. C., Kubas A., Steinhauer N., Wilson M. E., & van Engelsdorp D. (2018). Beekeeper stewardship, colony loss, and *Varroa destructor* management. Ambio, doi:10.1007/s13280-018-1130-z

[5] Rosenkranz P., Aumeier P., & Ziegelmann B. (2010). Biology and control of *Varroa destructor*. Journal of Invertebrate Pathology, 103, S96-S119, doi:10.1016/j.jip.2009.07.016.

[6] European Medicines Agency (EMA). (2010). Guideline on Veterinary Medicinal Products Controlling *Varroa destructor* Parasitosis in Bees (EMA/CVMP/EWP/459883/2008), Committee for Medicinal Products for Veterinary Use (CVMP). Retrieved from: www.ema.europa.eu

[7] Bendifallah L., Belguendouz R., Hamoudi L., & Arab K. (2018). Biological Activity of the *Salvia officinalis* L. (Lamiaceae) Essential Oil on *Varroa destructor* Infested Honeybees. Plants, 7(2), 44, doi:10.3390/plants7020044.

[8] Sabahi Q., Gashout H., Kelly P. G., & Guzman-Novoa E. (2017). Continuous release of oregano oil effectively and safely controls *Varroa destructor* infestations in honey bee colonies in a northern climate. Experimental and Applied Acarology, 72(3), 263-275, doi:10.1007/s10493-017-0157-3

The invention claimed is:

1. A kit for use in fighting *varroa* parasites, the kit comprising:
   a vaporizer device containing an essential oil mixture, the essential oil mixture comprising:
   15% to 25% wood vinegar by volume of the entire mixture;
   25% to 35% thyme oil by volume of the entire mixture;
   25% to 35% aniseed oil by volume of the entire mixture;
   8% to 13% clove oil by volume of the entire mixture;
   3% to 8% cardamom oil by volume of the entire mixture; and
   3% to 8% peppermint oil by volume of the entire mixture, wherein the essential oil mixture of the wood vinegar and the thyme oil and the aniseed oil and the clove oil and the cardamom oil and the peppermint oil does not exceed 100% by volume of the entire mixture.

2. The kit of claim 1, the essential oil mixture consisting essentially of:
   20% wood vinegar by volume of the entire mixture;
   30% thyme oil by volume of the entire mixture;
   30% aniseed oil by volume of the entire mixture;
   10% clove oil by volume of the entire mixture;
   5% cardamom oil by volume of the entire mixture; and
   5% peppermint oil by volume of the entire mixture.

3. The kit of claim 1, further comprising:
   a container receiving the essential oil mixture wherein said container is positioned in said vaporizer device.

4. The kit of claim 1, further comprising:
   a mat integrated with the essential oil mixture.

5. The kit of claim 4, wherein said mat contains copper therein.

6. The kit of claim 1, wherein said vaporizer device is a liquid vaporizer.

7. The kit of claim 6, wherein said liquid vaporizer device is selected from the group consisting of an e-cigarette and a mosquito-repellent electro-liquid device.

8. A method for fighting *varroa* parasites, the method comprising:
   placing an essential oil mixture into a vaporizing device, the essential oil mixture having 15% to 25% wood vinegar by volume of the entire mixture, 25% to 35% thyme oil by volume of the entire mixture, 25% to 35% aniseed oil by volume of the entire mixture, 8% to 13% clove oil by volume of the entire mixture, 3% to 8% cardamom oil by volume of the entire mixture, and 3% to 8% peppermint oil by volume of the entire mixture, wherein the essential oil mixture of the wood vinegar and the thyme oil and the aniseed oil and the clove oil and the cardamom oil and the peppermint oil does not have a volume exceeding 100% by volume of the entire mixture;
positioning the vaporizer device adjacent to a beehive;
activating the vaporizer device so as to cause the vapor therefrom to pass toward the beehive.

9. The method of claim 8, wherein the step of placing the essential oil mixture into the vaporizer device comprises:
placing the essential oil mixture into a chamber of the vaporizer device.

10. The method of claim 8, wherein the step of placing the essential oil mixture into the vaporizer device comprises:
placing a container containing the essential oil mixture into the vaporizer device.

11. The method of claim 8, wherein the step of placing the essential oil mixture into the vaporizer device comprises:
placing a mat impregnated with the essential oil mixture into the vaporizer device.

12. The method of claim 8, wherein the step of activating comprises:
manually switching an on-off button on the vaporizer device to an on position.

13. The method of claim 8, wherein the step of activating comprises:
using an application to remotely operate the vaporizer device.

\* \* \* \* \*